United States Patent [19]

Utsugi

[11] 4,148,307
[45] Apr. 10, 1979

[54] TUBULAR MEDICAL INSTRUMENT HAVING A FLEXIBLE SHEATH DRIVEN BY A PLURALITY OF CUFFS

[75] Inventor: Mikio Utsugi, Machida, Japan

[73] Assignee: Olympus Optical Company Limited, Tokyo, Japan

[21] Appl. No.: 753,487

[22] Filed: Dec. 22, 1976

[30] Foreign Application Priority Data

Dec. 26, 1975 [JP] Japan .......................... 50-179601[U]

[51] Int. Cl.$^2$ ............................................... A61B 1/00
[52] U.S. Cl. ..................................... 128/4; 128/2 M; 128/DIG. 9; 128/349 B
[58] Field of Search ........................................ 128/4-8, 128/2 M, DIG. 9, 349 R, 349 B, 348, 350 R

[56] References Cited

U.S. PATENT DOCUMENTS

| | | | |
|---|---|---|---|
| 2,855,934 | 10/1958 | Daughaday, Jr. | 128/349 R |
| 3,485,237 | 12/1969 | Bedford | 128/2 M |
| 3,665,928 | 5/1972 | Del Guercio | 128/350 R |
| 3,895,637 | 7/1975 | Choy | 128/348 |

FOREIGN PATENT DOCUMENTS

| | | | |
|---|---|---|---|
| 1170586 | 5/1964 | Fed. Rep. of Germany | 128/DIG. 9 |
| 1278965 | 11/1961 | France | 128/349 R |

Primary Examiner—Robert W. Michell
Assistant Examiner—Arthur S. Rose

[57] ABSTRACT

A tubular medical instrument has at least one cuff assembly including two cuffs disposed on the circumference of a flexible sheath, spaced at prescribed intervals and made expansible only in a radial direction of the flexible sheath and a deformable propellant cuff having a doubled-back section, disposed also on the circumference of the sheath between the two cuffs. When air is introduced into, or drawn from, the three cuffs selectively, the flexible sheath automatically advances step by step in the human body cavity.

9 Claims, 27 Drawing Figures

TUBULAR MEDICAL INSTRUMENT HAVING A FLEXIBLE SHEATH DRIVEN BY A PLURALITY OF CUFFS

BACKGROUND OF THE INVENTION

This invention relates to a tubular medical instrument such as a sound, catheter or endoscope having a flexible tube. Particularly, it relates to a tubular medical instrument having a cuff-equipped flexible sheath which is to be inserted into a human body cavity, for example stomach or small intestine, for a medical treatment.

Generally, the flexibble sheath of such tubular medical instrument advances deeper into the human body cavity, helped by the peristaltic movement of, for example, the small intestine. But it takes a long time to insert the flexible sheath in this manner. Thus, the sheath is often forced into the human body cavity by not only the peristaltic movement but also external force. If this is practiced, the patient suffers inevitably a greater pain.

To lessen such pain, the applicant has proposed in U.S. Pat. No. 4,066,070 issued Jan. 3, 1978 a tubular medical instrument having a flexible sheath which has a plurality of cuff assemblies on its forward portion. Each cuff assembly is constituted by a main cuff with a doubled-back section which can be deformed while held in rolling-contact with the wall of the body cavity and an auxiliary cuff disposed rearward of the main cuff and made expansible only in a radial direction of the sheath. Air is selectively introduced into these cuffs to expand them. The expanded cuffs broaden the body cavity. Then the operator inserts the sheath farther in the human body cavity. Since, there is no excessive friction between the sheath and the wall of the body cavity, the insertion of the sheath is smoothly carried out, without pressing the wall of the body cavity too hard.

SUMMARY OF THE INVENTION

An object of the invention is to provide a tubular medical instrument, which is more improved than the above-noted instrument of the applicant's own invention, and the sheath of which can advance or retreat in the body cavity without any manipulation.

An embodiment of this invention has at least one cuff assembly which is constituted by three cuffs arranged on a flexible sheath, a propellent cuff having a deformable, doubled-back section, a drive cuff disposed in front of the propellent cuff and made expansible only in the radial direction of the sheath, and a return cuff disposed behind the propellent cuff and made expansible only in the radial direction of the sheath. When the drive cuff is expanded, the doubled-back section of the propellent cuff which is in contact with the wall of the body cavity is forced backward. Then, in reaction to the movement of the doubled-back section the sheath advances deeper in the body cavity. When the return cuff is expanded, the doubled-back section of the propellent cuff is deformed to move forward without touching the wall of the body cavity. As the drive and return cuffs are repeatedly expanded alternately, the sheath advances deeper in the body cavity. Thus, the sheath can be inserted into the body cavity smoothly, with the wall of the body cavity not exerted with too strong a force. To carry out such an automatic sheath insertion, the operator needs only to supply a fluid selectively to the drive and return cuffs to expand the same. No skill is required in order to insert the sheath. The sheath can be easily and safely operated by an unskilled operator, too.

DESCRIPTION OF THE PREFERRED EMBODIMENTS

Figure 1:
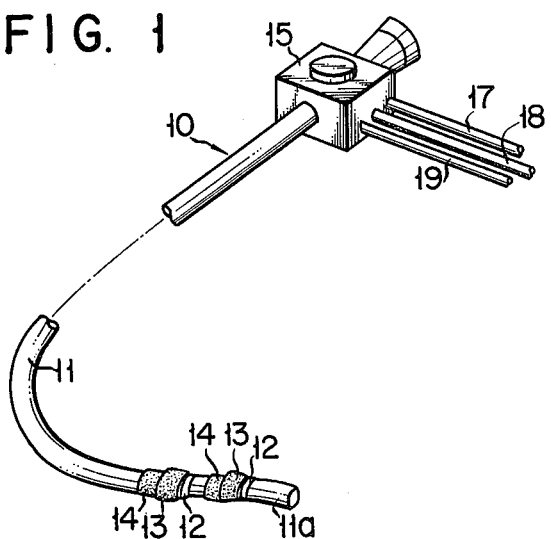
FIG. 1 is a partly omitted, perspective view of a tubular medical instrument provided with cuffs, according to a first embodiment of the invention.
Figure 3:
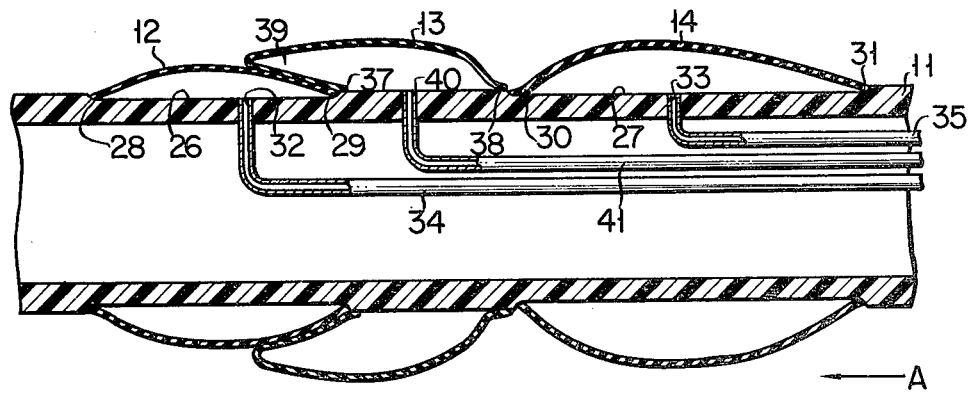
FIG. 3 is an enlarged, longitudinal cross-sectional view showing the forward portion of the sheath of the instrument as shown in FIG. 1.

The tubular medical instrument of FIG. 1 is an endoscope 10 provided with a flexible sheath 11. On the forward portion 11a of the sheath 11 there is fixed at least one cuff assembly constituted by a drive cuff 12, a propellent cuff 13 and a return cuff 14. These cuffs 12, 13 and 14 are so constructed as shown in FIG. 3 and as will be described later in detail.

Figure 2:
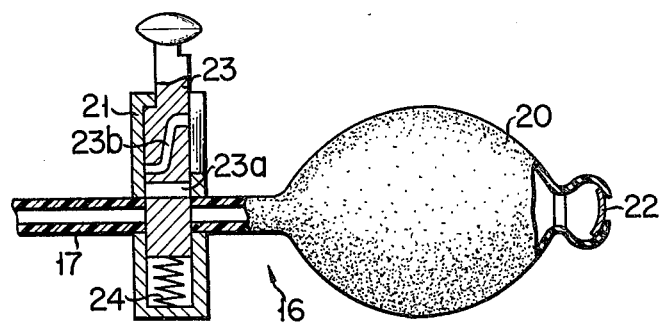
FIG. 2 is a partly cross-sectional, enlarged view of a fluid supply control device for supplying a fluid to, or drawing it from, the cuffs of the instrument as shown in FIG. 1.

Through the flexible sheath 11 a fluid is introduced into or drawn from these cuffs 12, 13 and 14 selectively. The fluid is supplied from, or returned to, a control section 15 also through the flexible sheath 11. The fluid supply is controlled by such a fluid supply control device 16 as shown in FIG. 2.

The fluid supply control device 16 communicates with the control section 15 through a pipe 17. Through this pipe 17 the fluid is supplied from the control section 15 to the drive cuff 12. Other two pipes 18 and 19 are connected at one end to the control section 15, while their other ends are connected respectively to devices (not shown) similar to the fluid supply control device 16. These pipes 18 and 19 serve to supply the fluid to the propellant cuff 13 and the return cuff 14, respectively.

The fluid supply control device 16 is to be manually operated. It has a pressure bulb 20 and a direction control valve 21 connected between the pipe 17 and the bulb 20. The bulb 20 has a check valve 22. The direction control valve 21 is provided with a valve member 23. In the valve member 23 there are formed a passage 23a through which the pipe 17 can communicate with the bulb 20 and another passage 23b through which the pipe 17 can communicate with the atmosphere. The direction control valve 21 further contains a spring 24 which normally pushes the valve member 23 upward. The operator depresses the valve member 23 from its closed position against the spring 24. When the passage 23a communicates with the pipe 17, the fluid, for example air, is supplied to the drive cuff 12 through the pipe 17. If the operator stops depressing the the valve member 23, the valve member 23 is urged by the spring 24 back to the closed position. Then, the compressed air in the pipe 17 has no way out. When the valve member 23 is depressed further to allow a communication between the pipe 17 and the passage 23b, the compressed air rushes out through the passage 23b into the atmosphere.

The flexible sheath 11 is to advance deeper in the human body cavity in the direction shown by arrow A in FIG. 3 or toward the forward portion of the sheath 11. On the circumference of the sheath 11 the drive cuff 12, the propellent cuff 13 and the return cuff 14 are arranged in this order away from the forward portion of the sheath 11. These cuffs 12, 13 and 14 are fixed to the sheath 11 in fluid-tight fashion by a suitable bonding agent.

On those portions of the circumference of the sheath 11 where the drive cuff 12 and return cuff 14 are fixed, two shallow, wide annular recesses 26 and 27 are formed, respectively. The drive cuff 12 and return cuff 14 are tubular members made of a resilient material such as rubber. The front end 28 and rear end 29 of the drive cuff 12 are secured in the annular recess 26, and the forward end 30 and rear end 31 of the return cuff 14 are secured in the corresponding annular recess 27. In the bottom of the annular recess 26 an air passage 32 is formed. Similarly, an air passage 33 is formed in the bottom of the annular recess 27. The air passages 32 and 33 communicate with air supply pipes 34 and 35, respectively.

These pipes 34 and 35 extend through the sheath 11 to the control section 15 and are connected to the pipes 17 and 19, respectively. The fluid supply control device 16 connected to the pipe 17 and the fluid supply control device (not shown) connected to the pipe 19 are so operated as to supply air to each drive cuff 12 and each return cuff 14 through the pipes 17 and 18, air supply pipes 34 and 35 and each air passage 32 and each air passage 33. As the air is introduced into them, the drive cuff 12 and the return cuff 14 are expanded gradually only in the radial direction of the sheath 11. When the air is drawn from the drive and return cuffs, the cuffs shrink by their own elasticity, and they are finally flattened in the annular recesses 26 and 27, respectively.

The propellent cuff 13 arranged between the drive cuff 12 and the return cuff 14 is made of a resilient material and shaped like a tube. Its front end 37 and rear end 38 are fixed on the circumference of the sheath 11 near the rear end 29 of the drive cuff 12 and the front end 30 of the return cuff 14, respectively. As shown in FIG. 3, the propellent cuff 13 has a doubled-back section (or folded back portion) 39. In other words, the propellent cuff 13 is folded along a circular line over the drive cuff 12 so as to form the doubled-back section 39. The doubled-back section 39 is extending forward (or to the left side in FIG. 3) and lies on the drive cuff 12 while the propellent cuff 13 is not exerted with any external force. The interior of the propellent cuff 13 is connected through an air passage 40 formed in the sheath 11 to one end of an air supply pipe 41 which extends through the sheath 11 along the air supply pipes 34 and 35. The other end of the air supply pipe 41 is connected to the pipe 18 at the control section 15. Thus, as the fluid supply control device 16 is operated, air is introduced into the propellent cuff 13 through the pipe 18, the air supply pipe 41 and the air passage 40. The propellent cuff 13 is then expanded to such an extent that the doubled-back section 39 maintains its shape.

Though not shown in FIG. 3, the air supply pipes 34, 35 and 41 are each branched within the sheath 11 in case two or more cuff assemblies are provided. Thus they can supply air to the drive cuffs 12, return cuffs 14 and propellent cuffs 13 of all the cuff assemblies at the same time.

With reference to FIGS. 4(a) to 4(j) it will be explained how the sheath 11 of FIG. 3 with two cuff assemblies advances deeper through the human body cavity.

Figure 4A:
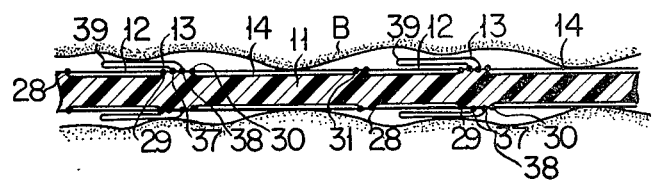
FIGS. 4(a) to 4(j) show various states of the cuffs mounted on the forward portion of the sheath shown in FIG. 3.
Figure 4B:
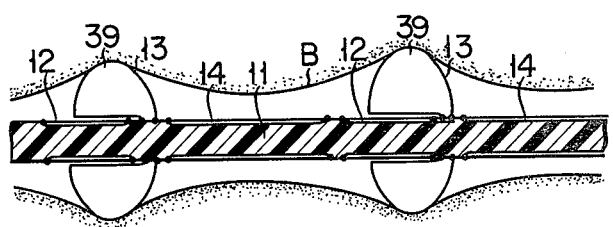
Figure 4C:
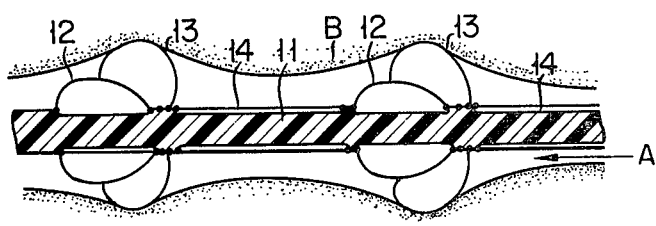
Figure 4D:
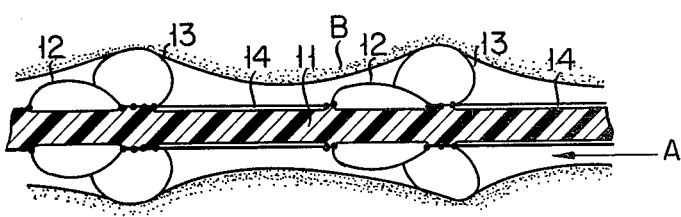

The operator inserts the sheath 11 into the patient's body cavity until it becomes difficult farther to insert the sheath 11 smoothly. At this stage, the cuffs of the sheath 11 are not expanded at all and are flattened on the circumference of the sheath 11 as shown in FIG. 4(a). Then, air is introduced into each propellent cuff 13. The propellent cuffs 13 are expanded to push the wall of the body cavity B to some extent, as showwn in FIG. 4(b). Thereafter, air is introduced into the drive cuffs 12. As the drive cuffs 12 are expanded gradually, they push the corresponding propellent cuffs 13, as shown in FIG. 4(c), in the radial direction of the sheath 11. As the drive cuffs 12 are further expanded, the doubled-back sections 39 of the corresponding propellent cuffs 13 are pushed backward as shown in FIG. 4(d). The drive cuffs 12 are further expanded until the doubled-back sections 39 are partly mounted on the corresponding return cuffs 14 as illustrated in FIG. 4(e).

Figure 4E:
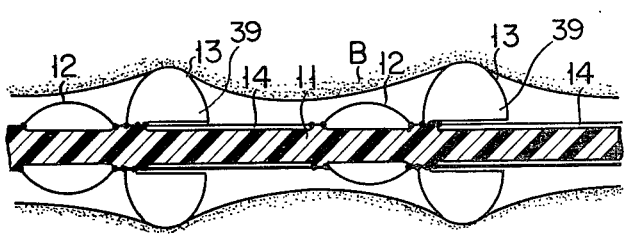

While each doubled-back section 39 is deformed by the corresponding drive cuff 12 gradually as shown in FIGS. 4(c) to 4(e), its surface is kept in a rolling contact with the wall of the body cvity, substantially with no slippage. During this period both doubled-back sections 39 keep on pushing the wall of the body cavity B away, i.e. to the upper-right corner of FIGS. 4(c) to 4(e). As a result, in reaction to the doubled-back sections 39 the sheath 11 advances smoothly for a distance in the direction of arrow A. During this one-step advance the sheath 11 does not directly touch the wall of the body cavity B, and no excessive friction occurs between the sheath 11 and the wall of the body cavity B. Thus the patient suffers no great pain.

Figure 4F:
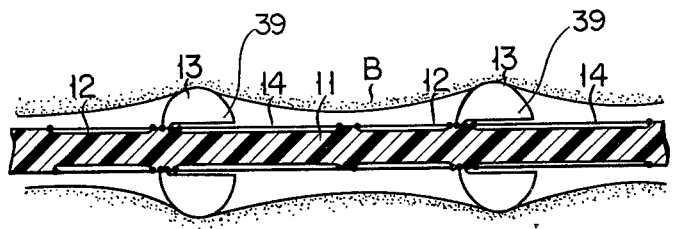

Upon completion of the one-step advance of the sheath 11, the air is drawn out of the drive cuffs 12 to flatten the same as shown in FIG. 4(f). Then, air is introduced into the return cuffs 14. As the return cuffs 14 are expanded gradually, the doubled-back sections 39 of the propellent cuffs 13 are pushed away from the sheath 11.

Figure 4G:
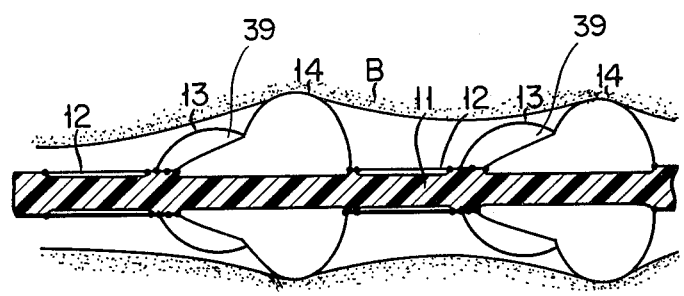
Figure 4H:
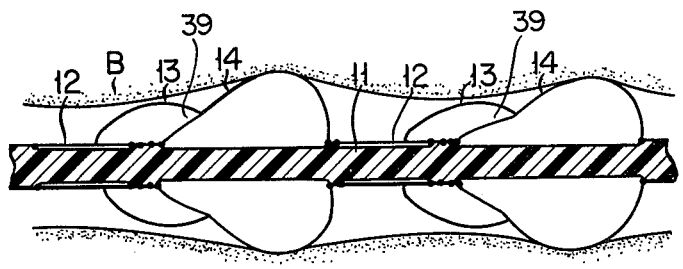
Figure 4I:
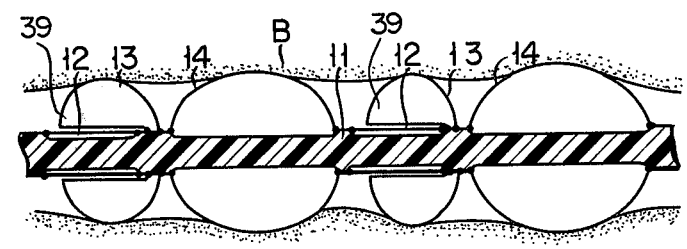

Thus, as shown in FIGS. 4(g) that part of each return cuff 14 which does not contact the corresponding doubled-back section 39 pushes the wall of the body cavity B until the doubled-back section 39 is released from the contact with the wall of the body cavity B. As the return cuffs 14 are further expanded, the doubled-back sections 39 are pushed onto the corresponding drive cuffs 12 as shown in FIG. 4(h). Finally the doubled-back sections 13 are fully mounted on the corresponding drive cuffs 12 as shown in FIG. 4(i).

Figure 4J:
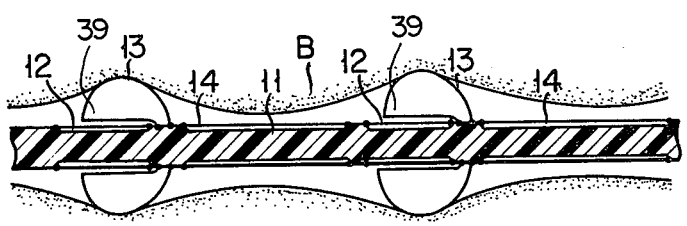

Thereafter, the air is drawn from each return cuff 14. Then the return cuffs 14 are brought into such a state as shown in FIG. 4(j), which is identical with the state shown in FIG. 4(b). This is the end of one cycle of cuff operation.

The cuff operation is repeated to make the sheath 11 advance step by step by itself until it reaches a desired position in the body cavity B. For this reason the operator need not force the sheath 11 into the body cavity. Since the circumference of the sheath 11 does not directly touch the wall of the body cavity B while it moves deeper in the body cavity B, no friction occurs between the sheath 11 and the wall of the body cavity B. As a result, the sheath 11 can advance smoothly and quickly, and the pain of the patient can be well lessened.

Figure 5:
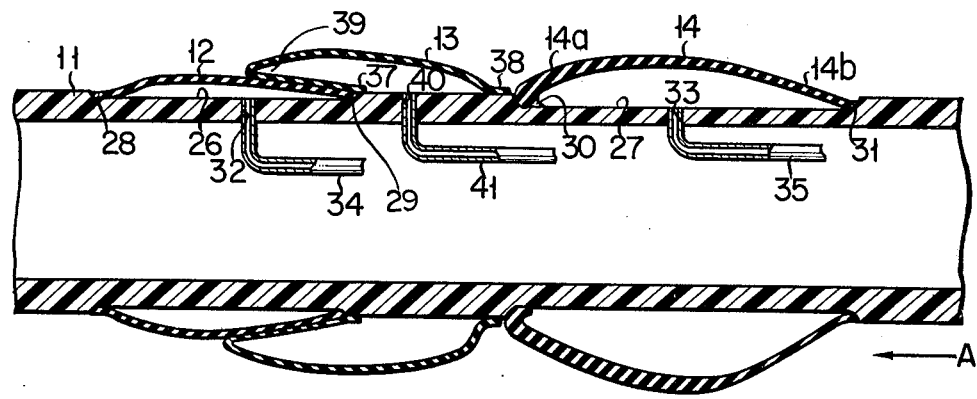
FIG. 5 is a longitudinal cross-sectional view of a second embodiment of the ivention.
Figure 6:
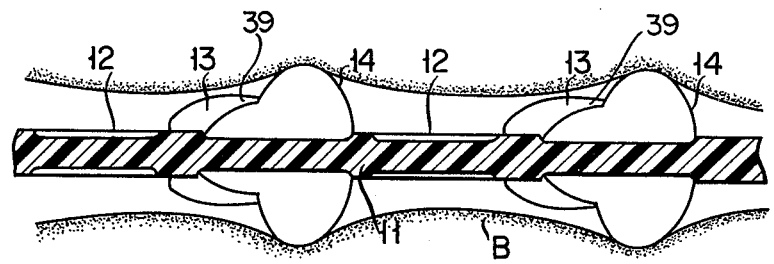
FIG. 6 is a schematical view, explaining how the cuffs mounted on the sheath of FIG. 5 are operated.

The second embodiment of the invention shown in FIG. 5 is constructionally similar to that of FIG. 1 except that in each cuff assembly the return cuff 14 is made increasingly thick toward a portion 14a adjacent to the propellent cuff 13. It is on the thick portion 14a of the return cuff 14 that the doubled-back section or folded back portion 39 of the propellent cuff 13 is to be mounted. In such a state as shown in FIG. 6 which corresponds to FIG. 4(g), the thin portion 14b of the return cuff 14 is more expanded than the thick portion 14a in the radial direction of a sheath 11. Thus, the thin portion 14b pushes away the wall of the body cavity B and braodens the body cavity B. Since the thick portion 14a of the return cuff 14 is not much expanded, the doubled-back section 39 of the propellent cuff 13 is not pushed so much away from the sheath 11. As a result, the doubled-back section 39 is spaced far from the wall of the body cavity B and can be readily deformed and moved onto the drive cuff 12.

Figure 7:
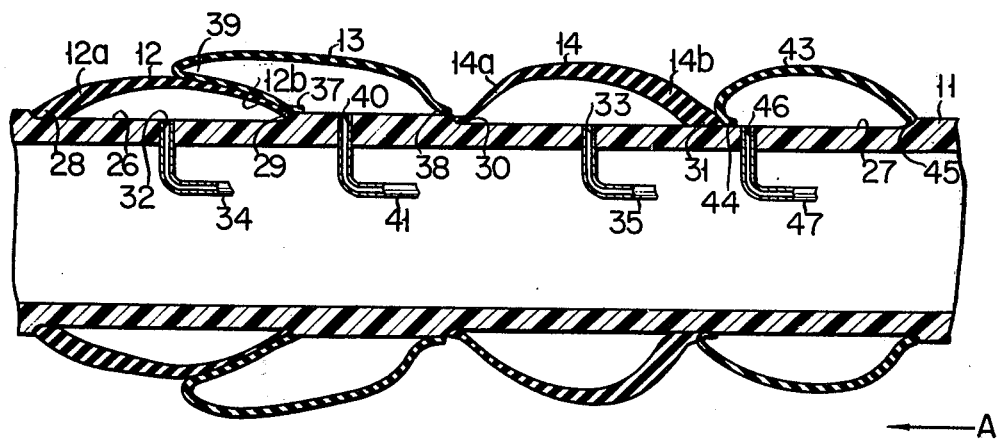
FIG. 7 is a longitudinal cross-sectional view of a third embodiment of the invention.
Figure 8A:
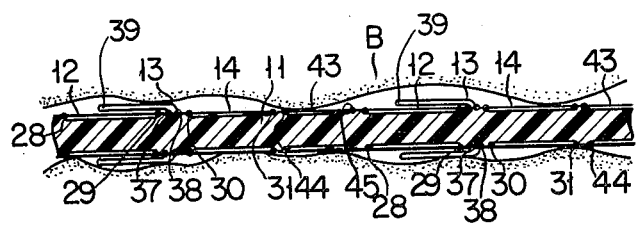
FIGS. 8(a) to 8(j) show various states of the cuffs mounted on the sheath shown in FIG. 7.
Figure 8B:
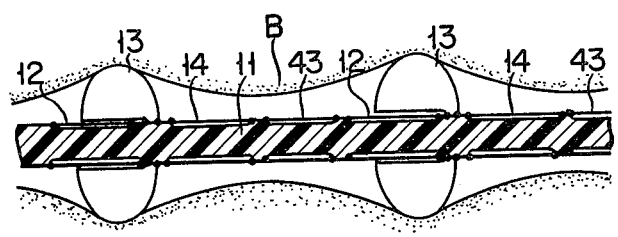
Figure 8C:
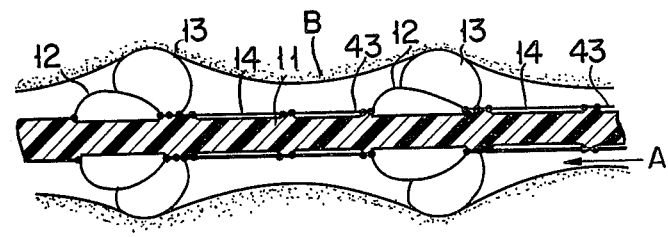
Figure 8D:
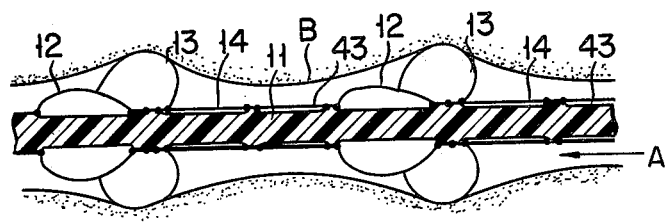
Figure 8E:
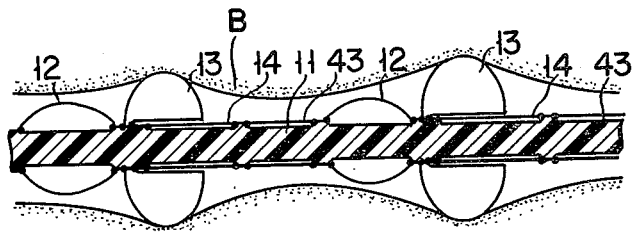
Figure 8F:
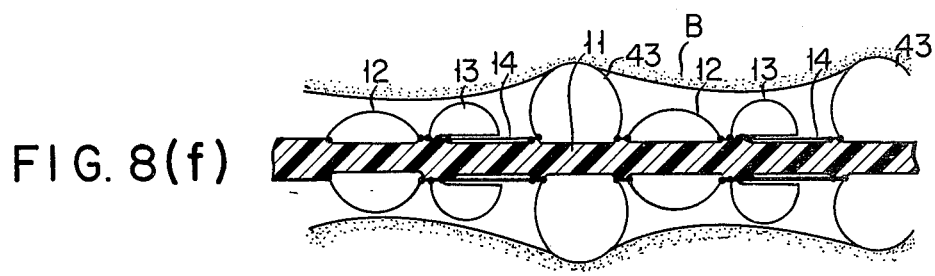
Figure 8G:
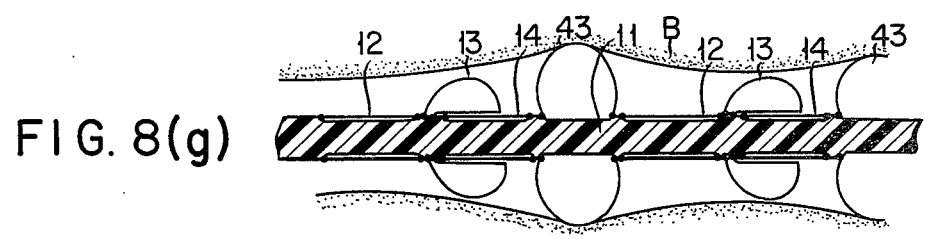
Figure 8H:
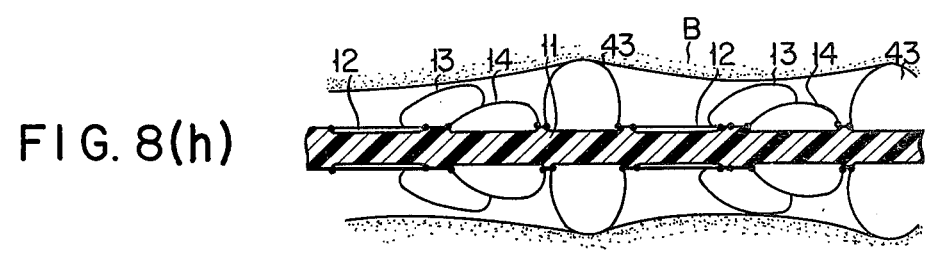
Figure 8I:
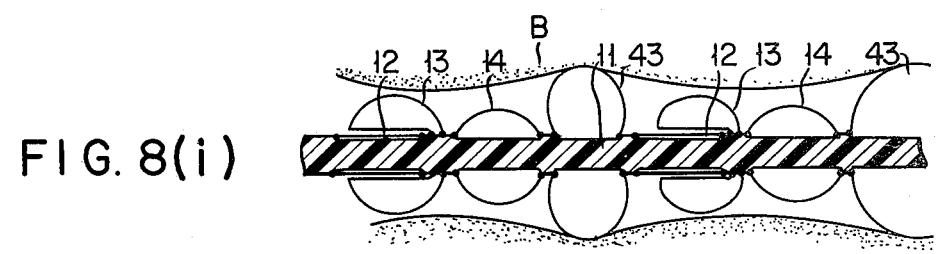
Figure 8J:
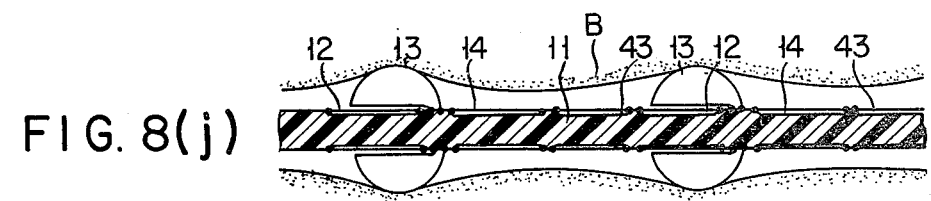

The third embodiment of the invention shown in FIG. 7 is identical with the embodiment of FIG. 1 except that each cuff assembly includes an auxiliary cuff 43 besides the drive cuff 12, propellent cuff 13 and return cuff 14. The auxiliary cuff 43 is disposed rearward of the return cuff 14. Like the other cuffs, it is a tubular member made of a resilient material and fixed in fluid-tight fashion to the circumference of a sheath 11 at the forward end 44 and the rear end 45. Its interior is connected through an air passage 46 formed in the sheath 11 to an air supply pipe 47. The air supply pipe 47 extends through the sheath 11 to a control section 15. Thus, through the air supply pipe 47 and the air passage 46 air can be supplied to the auxiliary cuff 43.

In this embodiment, the return cuff 14 off each cuff assembly is made increasingly thick toward its rear end 31. Thus, as air is introduced into the return cuff 14, the thin portion 14a of the return cuff 14 is expanded more than the thick portion 14b. As a result, the doubled-back section 39 of the propellent cuff 13, if mounted on the thin portion 14a of the return cuff 14, is deformed and moved smoothly toward the drive cuff 12. Unlike those of the embodiments shown in FIGS. 1 and 5, each return cuff 14 of this embodiment serves only to move the doubled-back section or folded back portion 39 toward the drive cuff 12. It need not push the wall of the human body cavity B to broaden the body cavity B, because the auxiliary cuff 43 is to be expanded to broaden the body cavity B.

As shown in FIG. 7, each drive cuff 12 is made increasingly thick toward its front end 28. For this reason, as air is introduced into the drive cuff 12, the thin portion 12b of the drive cuff 12 is expanded more than the thick portion 12a. Thus, the doubled-back section 39 of the propellent cuff 13, if mounted on the thin portion 12b of the drive cuff 12, is deformed and moved smoothly toward the return cuff 14.

Air is selectively introduced into, and drawn from, the cuffs of both cuff assemblies in such a manner as illustrated in FIGS. 8(a) to 8(j). Each cycle of cuff operation makes the sheath 11 advances deeper in the body cavity B for a specific distance. If the cuff operation is made repeatedly, the sheath 11 advances step by step in the body cavity B.

Figure 9:
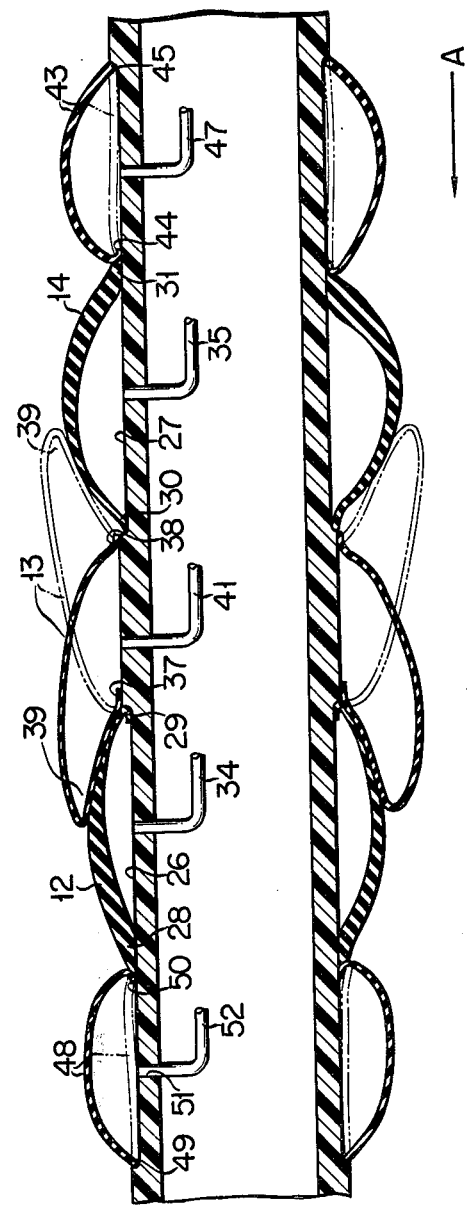
FIG. 9 is a longitudinal cross-sectional view of a fourth embodiment of the invention.

The fourth tubular medical instrument shown in FIG. 9 has a flexible sheath 11 which can not only advance by itself but also retreat by itself in the body cavity. This embodiment is identical with the embodiment of FIG. 7 except that each cuff assembly is provided with a retreat drive cuff 48 in addition to the drive cuff 12, propellent cuff 13, return cuff 14 and auxiliary cuff 43. The return drive cuff 48 is fixed on the sheath 11 in front of the drive cuff 12.

In each cuff assembly of this embodiment, like the auxiliary cuff 43, the retreat drive cuff 48 is a tubular member the plate thickness of which is substantially uniform and is expansible only in the radial direction of the sheath 11. Like the other cuffs, the retreat drive cuff 48 is made of a resilient material and fixed to the circumference of the sheath 11 at its front end 49 and its rear end 50 in fluid-tight fashion. Its interior is connected through an air passage 51 formed in the sheath 11 to one end of an air supply pipe 52. The air supply pipe extends through the sheath 11, and its other end is connected to a control section 15. Thus, air can be supplied from the control section 15 to the retreat drive cuff 48 through the air supply pipe 52 and the air passage 51.

As shown in FIG. 9, in ech cuff assembly the retreat drive cuff 48 and the drive cuff 12 are arranged in the lengthwise direction of the sheath 11 symmetrically to the return cuff 14 and the auxiliary cuff 43 with respect to the propellent cuff 13. If air is repeatedly introduced into, and drawn from, the cuffs of this embodiment other than the retreat drive cuffs 48 as done in the embodiment of FIG. 7, the sheath 11 advances step by step deeper in the body cavity in the direction of arrow A. During the advance of the sheath 11 the retreat drive cuffs 48 is not expanded at all.

To cause the sheath 11 to retreat in the body cavity in the opposite direction to arrow A, the auxiliary cuff 43 is deflated first. Then, the retreat drive cuff 48 is expanded just enough to push the wall of the body cavity, thus broadening the body cavity. Next, the drive cuff 12 is expanded to deform the propellent cuff 13 gradually. As the propellent cuff 13 is deformed, its doubled-back section or folded back portion 39 moves toward the return cuff 14 and is finally mounted onto the return cuff 14 as indicated by chain lines in FIG. 9.

Thereafter, the return cuff 12 is expanded in the same manner as the drive cuff 12 is during the advance of the sheath 11. Similarly, the drive cuff 12 is expanded in the same manner as the return cuff 14 is during the advance of the sheath 11. Further, the retreat drive cuff 48 is expanded in the same manner as the auxiliary cuff 43 is during the advance of the sheath 11. In this manner the drive cuff 12, return cuff 14 and retreat drive cuff 48 are repeatedly expanded, thereby causing the sheath 11 to retreat in the body cavity. Though not explained herein, it will be well understood how the propellent cuff 13 moves to make the sheath 11 retreat.

What is claimed is:
1. A tubular medical instrument comprising:
   a flexible sheath to be inserted into a human body cavity, at least one flexible tubular propellent cuff having end portions, said end portions being mounted on the outer surface of said sheath and adapted to contain a fluid, means for supplying fluid to said propellent cuff, tubular drive cuff disposed adjacent to said propellent cuff on the outer surface of said sheath,
   a tubular return cuff disposed adjacent to said propellent cuff and opposite to said drive cuff with respect to said propellent cuff, said drive and return cuffs being adapted alternately to have a fluid supplied thereinto to expand radially and drawn therefrom to be flattened, means for supplying and withdrawing fluid from said drive and return cuffs, and said propellent cuff having a width greater than the distance between said mounted end portions such that said propellent cuff is normally folded along a circular line over a flattened one of said drive and return cuffs with a folded back portion of said propellent cuff lying on said flattened one of said drive and return cuffs, said propellent cuff being progressively deformed toward the other of said drive and return cuffs with the outer surface of said propellent cuff kept in contact with the inner surface of said human body cavity as fluid is introduced into said one of said drive and return cuffs and drawn from said other of said drive and return cuffs, and being finally folded along another circular line over said other of said drive and return cuffs with a newly folded back portion lying on said other drive and return cuffs now flattened, said propellent cuff being adapted to move said tubular instrument in said human body cavity in the opposite direction to the direction in which said propellent cuff is deformed progressively.

2. The tubular medical instrument according to claim 1, whherein said return cuff is gradually thicker toward an end thereof which is remote from said propellent cuff.

3. The tubular medical instrument according to claim 1, wherein said drive cuff is gradually thicker toward an end thereof which is remote from said propellent cuff.

4. The tubular medical instrument according to claim 1, wherein said drive cuff and return cuff are gradually thicker toward that end thereof which is remote from said propellent cuff.

5. The tubular medical instrument according to claim 1, wherein a tubular auxiliary cuff is mounted on that outer surface portion of said sheath which is adjacent to that end of said return cuff and which is remote from said propellent cuff, there is means for supplying fluid to said auxiliary cuff, said auxiliary tubular cuff being radially expanded by introduction of a fluid thereinto for broadening said body cavity while said propellent cuff is moved from said return cuff toward said drive cuff.

6. The tubular medical instrument according to claim 5, wherein said drive cuff and return cuff are gradually thicker toward that end of said drive and return cuffs which is remote from said propellent cuff.

7. The tubular medical instrument according to claim 5, wherein a tubular retreat cuff is mounted on that outer surface portion of said sheath which is adjacent to that end of said drive cuff which is remote from said propellent cuff, and there is means for supplying fluid to said retreat cuff, said retreat cuff being radially expanded by introduction of a fluid thereinto for broadening said body cavity while said propellent cuff is moved from said drive cuff toward said return cuff and while said auxiliary cuff remains flat.

8. The tubular medical instrument according to claim 5, wherein said drive cuff and return cuff are gradually thicker toward that end thereof which is remote from said propellent cuff.

9. The tubular medical instrument according to claim 1, wherein said return cuff is gradually thicker toward an end thereof which is adjacent to said propellent cuff.

* * * * *